US008197865B2

(12) United States Patent
Glynn et al.

(10) Patent No.: US 8,197,865 B2
(45) Date of Patent: Jun. 12, 2012

(54) METHODS AND COMPOSITIONS FOR MODULATING HAIR GROWTH OR REGROWTH

(75) Inventors: Kelly M. Glynn, Grand Rapids, MI (US); Lane A. Duvel, Rockford, MI (US); David M. Flower, Grand Rapids, MI (US)

(73) Assignee: Access Business Group International LLC, Ada, MI (US)

( * ) Notice: Subject to any disclaimer, the term of this patent is extended or adjusted under 35 U.S.C. 154(b) by 45 days.

(21) Appl. No.: 12/901,761

(22) Filed: Oct. 11, 2010

(65) Prior Publication Data

US 2011/0059192 A1 Mar. 10, 2011

Related U.S. Application Data

(63) Continuation-in-part of application No. 11/500,704, filed on Aug. 8, 2006, now abandoned.

(60) Provisional application No. 60/706,930, filed on Aug. 9, 2005.

(51) Int. Cl.

| | |
|---|---|
| ***A61K 36/00*** | (2006.01) |
| ***A61K 36/236*** | (2006.01) |
| ***A61K 36/324*** | (2006.01) |
| ***A61K 36/488*** | (2006.01) |
| ***A61K 36/82*** | (2006.01) |
| ***A61K 36/31*** | (2006.01) |
| ***A61K 36/48*** | (2006.01) |

(52) U.S. Cl. ........ 424/727; 424/725; 424/729; 424/757; 424/755

(58) Field of Classification Search ........................ None
See application file for complete search history.

(56) References Cited

U.S. PATENT DOCUMENTS

| | | | | |
|---|---|---|---|---|
| 2002/0028257 | A1 | 3/2002 | Catalfo et al. | |
| 2005/0119243 | A1 | 6/2005 | Harris et al. | |
| 2005/0260152 | A1 * | 11/2005 | Jaghab | 424/74 |
| 2005/0271596 | A1 | 12/2005 | Friedman et al. | |
| 2006/0216255 | A1 | 9/2006 | Lee et al. | |

FOREIGN PATENT DOCUMENTS

| | | |
|---|---|---|
| EP | 1541152 | 6/2005 |
| JP | 05310537 | 11/1993 |
| JP | 05310537 A * | 11/1993 |
| JP | 2004307443 | 11/2004 |
| WO | WO 03/072049 | 9/2003 |
| WO | WO 03/105791 | 12/2003 |
| WO | WO 03105791 A1 * | 12/2003 |
| WO | WO 2005/041854 | 5/2005 |
| WO | WO 2005041854 A2 * | 5/2005 |

OTHER PUBLICATIONS

Genistil-R and Genistil-RM-new topical phytoestrogen based products; Lipoxidil—The New Generation of Hairloss Treatment; Innovative Hairloss Therapy with Liposomes, 2005, pp. 1-3, http://www.lipoxidil.com/site/phytoestrogens.php.

Stenn, "Laboratory Assessment of Hair Follicle Growth", *Skin Pharmacol Appl Skin Physiol*, No. 12, 1999, pp. 154-157.

Wikipedia, (http://en.wikipedia.org/wiki/Perilla_frutescens), Perilla frutescens, Nov. 20, 2006.

* cited by examiner

*Primary Examiner* — Qiuwen Mi

(74) *Attorney, Agent, or Firm* — Brinks Hofer Gilson & Lione; G. Peter Nichols

(57) ABSTRACT

The present invention relates to compositions and methods for modulating hair growth or regrowth. The compositions of the present invention include extracts of one or more of the following: *Boswellia serrata, Undaria pinnatifida*, green tea (e.g., *Camellia sinensis*), shiso, *Purerariamirifica*, luteolin (e.g. *Perilla ocymoides* leaf extract), astilbin, vitamin E, amentoflavone, tetrahydropiperine, lichochalcone, astaxanthin, red clover, *Brassica juncea*, unfermented green rooibos, enzyme CoQ10, salvia, ximenynic acid, hops oleoresin, apple, soy, saw palmetto, or ellagic extract, or any derivative thereof.

6 Claims, 1 Drawing Sheet

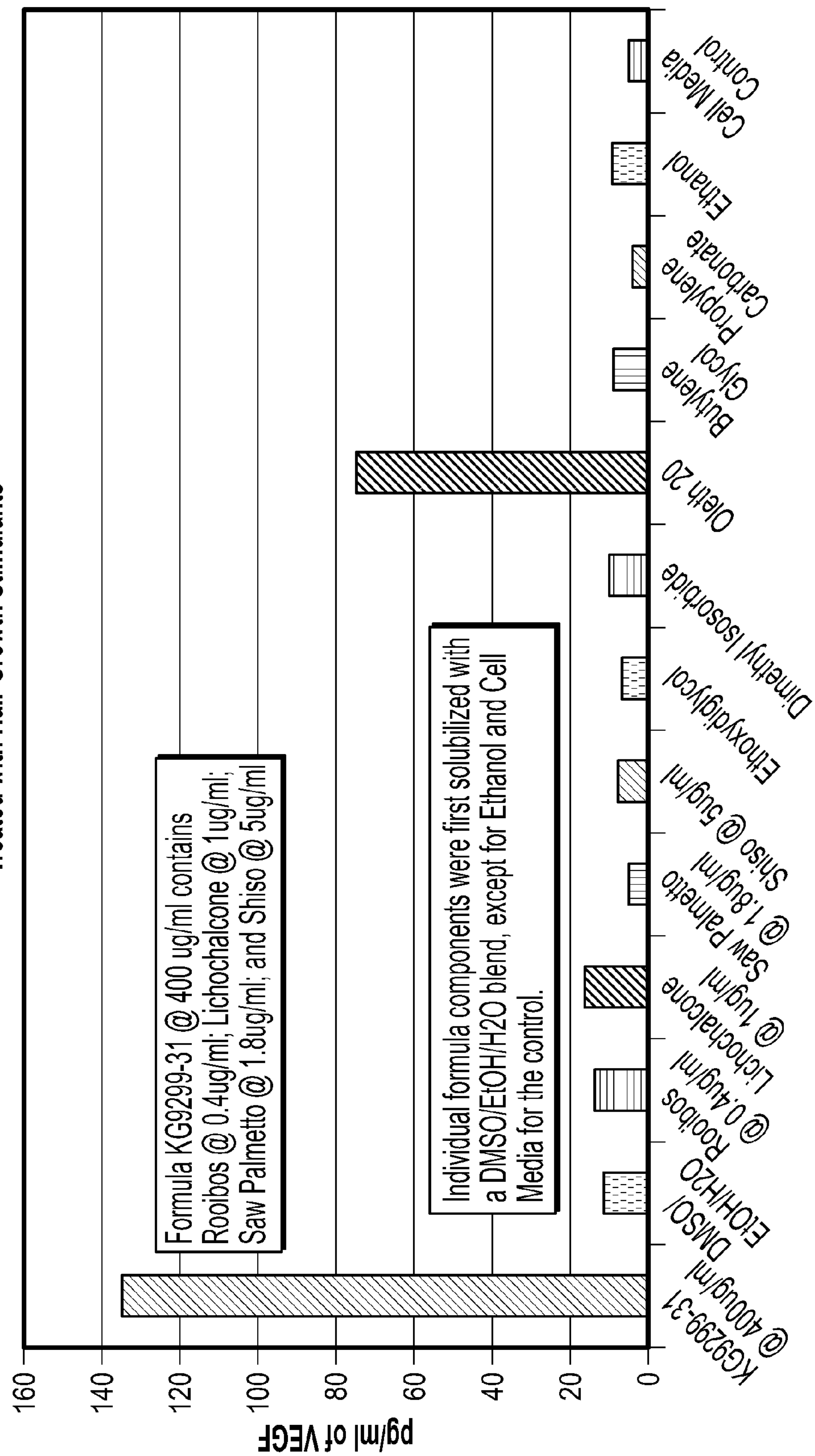
VEGF Protein Expression from a HFDPC & HEK Co-Culture
Treated with Hair Growth Stimulants
pg/ml of VEGF
160
140
120
100
80
60
40
20
0
Formula KG9299-31 @ 400 ug/ml contains Rooibos @ 0.4ug/ml; Lichochalcone @ 1ug/ml; Saw Palmetto @ 1.8ug/ml; and Shiso @ 5ug/ml
Individual formula components were first solubilized with a DMSO/EtOH/H2O blend, except for Ethanol and Cell Media for the control.
KG9299-31 @ 400ug/ml
DMSO/ EtOH/H2O
Rooibos @ 0.4ug/ml
Lichochalcone @ 1ug/ml
Saw Palmetto @ 1.8ug/ml
Shiso @ 5ug/ml
Ethoxydiglycol
Dimethyl Isosorbide
Oleth 20
Butylene Glycol
Propylene Carbonate
Ethanol
Cell Media Control

METHODS AND COMPOSITIONS FOR MODULATING HAIR GROWTH OR REGROWTH

This application is a continuation-in-part of U.S. application Ser. No. 11/500,704 filed Aug. 8, 2006, (now abandoned) which claims priority to U.S. Provisional Application Ser. No. 60/706,930, filed Aug. 9, 2005, the entire contents of both are incorporated herein by reference.

BACKGROUND

The average human scalp contains over 100,000 hair follicles and loses 50 to 100 hairs per day as normal hair fallout. In subjects with male pattern alopecia, a bald area will contain about two-thirds to three-fourths the number of hairs compared to a normal scalp area.

Alopecia affects both males and females and may result from genetic factors, auto-immune disorder, chemotherapy, aging, or local or systemic disease. It can also occur in a number of areas of the body, such as the face, trunk, scalp and limbs. Causes of hair loss can be grouped into the following categories:

Male or Female Pattern Baldness

This type of hair loss requires the presence of male or female hormones, e.g. androgens, but the cause is unknown. The extent of hair loss in any male greatly depends on the genes he inherits from his father, mother, or both. Hair loss begins at the temples or at the top of the head. If male pattern hair loss begins in the mid-teens, subsequent hair loss is usually fairly extensive. Male balding goes in waves. Hair loss may begin in the early 20's, then stop, only to start again in a few years. By the age of 20 to 30 years, 30% of men have bald spots. This continues to rise until age 50-60, when 50% of men are completely bald.

The rate of hair loss is affected by advancing age, the tendency to bald early due to inherited genes, and an overabundance of the male hormone dihydrotestosterone (DHT) within the hair follicle. DHT acts on a hormone receptor within the hair follicle, and thereby slows hair production and produces weak, shorter hair. Sometimes DHT production even stops hair growth completely. Although balding men have above average amounts of DHT in their hair follicles, they usually do not have above average circulating testosterone levels.

Female pattern baldness is not as common as male pattern baldness, but is on the rise. It is confined to the hair predominantly at the top of the head and complete baldness is rare in females.

Toxic Alopecia

This type of hair loss is temporary but typically lasts three to four months, and often is caused by an infectious disease. For example, toxic alopecia may occur as a result of hypothyroidism, diabetes, hormonal problems, vitamin deficiencies, hypopituitarism, parasites, poor digestion, early stage of syphilis, vitamin A or retinoid overdoses, or other cytotoxic drugs.

Alopecia Areata

This is a sudden hair loss in demarcated areas. It can affect any hairy area, but most frequently affects the scalp and beard. Hair loss confined to a few areas is often reversed in a few months even without treatment but recurrence is a possibility. Alopecia areata usually occurs in people with no obvious skin disease or systemic disease, but in rare cases lab tests may show anti-microsomial antibodies to thyroglobulin, gastric parietal cells and adrenal cells.

Scarring Alopecia

Scarring alopecia results from inflammation and tissue destruction. It may be due to injuries such as burns, physical trauma, or destruction after xrays. In these cases, little regrowth is expected. Other causes are cutaneous lupus erythematosus, lichen planus, chronic deep bacterial or fungal infections, deep ulcers, sarcoidosis, syphilis, or tuberculosis. Slow growing tumors of the scalp are a rare cause of hair loss.

While none of these conditions is very well understood, each condition is distressing because hair is often considered an important factor in human social communications and interactions.

Numerous approaches have been suggested for treating hair loss. Two of the most commonly used and accepted compounds for preventing hair loss are minoxidil, the active ingredient in Rogaine® and the 5α-reductase inhibitor, finasteride, the active ingredient in Propecia®. However, cosmetic treatment of age-related hair loss in patients with topical solution of minoxidil or finasteride has resulted in only moderate regrowth of hair in less than 40% of such patients. Indeed, less than ten percent of the men who use Rogaine® achieve satisfactory results. Thus, there is a need in the art for more effective methods of and compositions for treating hair loss. Preferably, new methods and compositions will require fewer applications of active ingredients; provide hair regrowth sooner, in more abundance, and thicker, than presently observed with minoxidil or finasteride treatment.

BRIEF SUMMARY

In one embodiment, the present invention is a composition for preventing or decreasing the loss of hair and/or for stimulating or increasing hair growth or regrowth, wherein the composition comprises one or more of the following ingredients in an effective amount: *boswellia serrata* extract (e.g. frankincense), Boswellin Forte®, boswin 30 (5-loxin), *Undaria pinnatifida* extract (e.g. an extract of brown algae such as GFS 75%), extracts of green tea or extracts of *Camellia sinensis* leaf (e.g. extracts of Teavigo™, Teavigo™ phospholipids (epigallocatechin gallate (EGCG)), shiso extract, *Pureraria mirifica* extract, luteolin (e.g., *Perilla ocymoides* leaf extract), astilbin, extracts or derivatives of vitamin E (e.g. Vital ET™ or disodium lauraminodipropionate tocopheryl phosphate), amentoflavone, tetrahydropiperine (e.g. Cosmoperine™), lichochalcone (LR15 (glycyrrhiza inflata root extract)), astaxanthin, *Brassica juncea* extract (e.g., Phytavail™ Zn), red clover extract, unfermented green rooibos extract, enzyme CoQ-10, salvia extract (e.g. an extract of *Salvia miltorrhiza*), ximenynic acid extract, hops oleoresin extract, apple extract, soy extract, saw palmetto extract, or ellagic acid extract.

In another embodiment, the present invention is method of preventing or decreasing hair loss and/or stimulating or increasing hair growth or regrowth, wherein the method comprises administering a composition comprising one or more of the following ingredients in an effective amount for a period of time sufficient to bring about the desired effect: *boswellia serrata* extract (e.g. frankincense), Boswellin Forte®, boswin 30 (5-loxin), *Undaria pinnatifida* extract (e.g. an extract of brown algae such as GFS 75%), extracts of green tea or extracts of *Camellia sinensis* leaf (e.g. extracts of Teavigo™, Teavigo™ phospholipids (epigallocatechin gallate (EGCG)), shiso extract, *Pureraria mirifica* extract, luteolin (e.g., *Perilla ocymoides* leaf extract), astilbin, extracts or derivatives of vitamin E (e.g. Vital ET™ or disodium lauraminodipropionate tocopheryl phosphate), amentoflavone, tetrahydropiperine (e.g. Cosmoperine™), lichochalcone (LR15 (glycyrrhiza inflata root extract)), astaxanthin, *Brassica juncea* extract (e.g., Phytavail™ Zn), red clover extract, unfermented green rooibos extract, enzyme CoQ-10, salvia extract (e.g. an extract of *Salvia miltorrhiza*), ximenynic acid extract, hops oleoresin extract, apple extract, soy extract, saw palmetto extract, or ellagic acid extract.

In a further embodiment, the present invention is a composition for treating hair loss, wherein the composition of the present invention inhibits synthesis of dihydrotestosterone, and comprises one or more of the following ingredients in an effective amount: *boswellia serrata* extract (e.g. frankincense), Boswellin Forte®, boswin 30 (5-loxin), *Undaria pinnatifida* extract (e.g. an extract of brown algae such as GFS 75%), extracts of green tea or extracts of *Camellia sinensis* leaf (e.g. extracts of Teavigo™, Teavigo™ phospholipids (epigallocatechin gallate (EGCG)), shiso extract, *Purerria mirifica* extract, luteolin (e.g., *Perilla ocymoides* leaf extract), astilbin, extracts or derivatives of vitamin E (e.g. Vital ET™ or disodium lauraminodipropionate tocopheryl phosphate), amentoflavone, tetrahydropiperine (e.g. Cosmoperine™), lichochalcone (LR15 (glycyrrhiza inflata root extract)), astaxanthin, *Brassica juncea* extract (e.g., Phytavail™ Zn), red clover extract, unfermented green rooibos extract, enzyme CoQ-10, salvia extract (e.g. an extract of *Salvia miltorrhiza*), ximenynic acid extract, hops oleoresin extract, apple extract, soy extract, saw palmetto extract, or ellagic acid extract.

In another embodiment, the present invention is a method of treating hair loss comprising administering a composition comprising one or more of the following ingredients in an effective amount: *boswellia serrata* extract (e.g. frankincense), Boswellin Forte®, boswin 30 (5-loxin), *Undaria pinnatifida* extract (e.g. an extract of brown algae such as GFS 75%), extracts of green tea or extracts of *Camellia sinensis* leaf (e.g. extracts of Teavigo™, Teavigo™ phospholipids (epigallocatechin gallate (EGCG)), shiso extract, *Pureraria mirifica* extract, luteolin (e.g., *Perilla ocymoides* leaf extract), astilbin, extracts or derivatives of vitamin E (e.g. Vital ET™ or disodium lauraminodipropionate tocopheryl phosphate), amentoflavone, tetrahydropiperine (e.g. Cosmoperine™), lichochalcone (LR15 (glycyrrhiza inflata root extract)), astaxanthin, *Brassica juncea* extract (e.g., Phytavail™ Zn), red clover extract, unfermented green rooibos extract, enzyme CoQ-10, salvia extract (e.g. an extract of *Salvia miltorrhiza*), ximenynic acid extract, hops oleoresin extract, apple extract, soy extract, saw palmetto extract, or ellagic acid extract, wherein administration of the composition inhibits synthesis of dihydrotestosterone.

In a further embodiment, the present invention is a composition for treating hair loss, wherein the composition of the present invention increases secretion of Keratinocyte Growth Factor (KGF) and/or Vascular Endothelial Growth Factor (VEGF) and wherein the composition comprises one or more of the following ingredients in an effective amount: *boswellia serrata* extract (e.g. frankincense), Boswellin Forte®, boswin 30 (5-loxin), *Undaria pinnatifida* extract (e.g. an extract of brown algae such as GFS 75%), extracts of green tea or extracts of *Camellia sinensis* leaf (e.g. extracts of Teavigo™, Teavigo™ phospholipids (epigallocatechin gallate (EGCG)), shiso extract, *Pureraria mirifica* extract, luteolin (e.g., *Perilla ocymoides* leaf extract), astilbin, extracts or derivatives of vitamin E (e.g. Vital ET™ or disodium lauraminodipropionate tocopheryl phosphate), amentoflavone, tetrahydropiperine (e.g. Cosmoperine™), lichochalcone (LR15 (glycyrrhiza inflata root extract)), astaxanthin, *Brassica juncea* extract (e.g., Phytavail™ Zn), red clover extract, unfermented green rooibos extract, enzyme CoQ-10, salvia extract (e.g. an extract of *Salvia miltorrhiza*), ximenynic acid extract, hops oleoresin extract, apple extract, soy extract, saw palmetto extract, or ellagic acid extract.

In another embodiment, the present invention is a method of treating hair loss comprising administering a composition comprising one or more of the following ingredients in an effective amount: *boswellia serrata* extract (e.g. frankincense), Boswellin Forte®, boswin 30 (5-loxin), *Undaria pinnatifida* extract (e.g. an extract of brown algae such as GFS 75%), extracts of green tea or extracts of *Camellia sinensis* leaf (e.g. extracts of Teavigo™, Teavigo™ phospholipids (epigallocatechin gallate (EGCG)), shiso extract, *Pureraria mirifica* extract, luteolin (e.g., *Perilla ocymoides* leaf extract), astilbin, extracts or derivatives of vitamin E (e.g. Vital ET™ or disodium lauraminodipropionate tocopheryl phosphate), amentoflavone, tetrahydropiperine (e.g. Cosmoperine™), lichochalcone (LR15 (glycyrrhiza inflata root extract)), astaxanthin, *Brassica juncea* extract (e.g., Phytavail™ Zn), red clover extract, unfermented green rooibos extract, enzyme CoQ-10, salvia extract (e.g. an extract of *Salvia miltorrhiza*), ximenynic acid extract, hops oleoresin extract, apple extract, soy extract, saw palmetto extract, or ellagic acid extract, wherein administration of the composition increases secretion of KGF and/or VEGF.

In a further embodiment, the present invention is a composition for treating hair loss, wherein the composition of the present invention inhibits proteasomal activity and/or interleukin-1 (IL-1) activity, and comprises one or more of the following ingredients in an effective amount: *boswellia serrata* extract (e.g. frankincense), Boswellin Forte®, boswin 30 (5-toxin), *Undaria pinnatifida* extract (e.g. an extract of brown algae such as GFS 75%), extracts of green tea or extracts of *Camellia sinensis* leaf (e.g. extracts of Teavigo™, Teavigo™ phospholipids (epigallocatechin gallate (EGCG)), shiso extract, *Pureraria mirifica* extract, luteolin (e.g., *Perilla ocymoides* leaf extract), astilbin, extracts or derivatives of vitamin E (e.g. Vital ET™ or disodium lauraminodipropionate tocopheryl phosphate), amentoflavone, tetrahydropiperine (e.g. Cosmoperine™), lichochalcone (LR15 (glycyrrhiza inflata root extract)), astaxanthin, *Brassica juncea* extract (e.g., Phytavail™ Zn), red clover extract, unfermented green rooibos extract, enzyme CoQ-10, salvia extract (e.g. an extract of *Salvia miltorrhiza*), ximenynic acid extract, hops oleoresin extract, apple extract, soy extract, saw palmetto extract, or ellagic acid extract.

In another embodiment, the present invention is a method of treating hair loss comprising administering a composition comprising one or more of the following ingredients in an effective amount: *boswellia serrata* extract (e.g. frankincense), Boswellin Forte®, boswin 30 (5-loxin), *Undaria pinnatifida* extract (e.g. an extract of brown algae such as GFS 75%), extracts of green tea or extracts of *Camellia sinensis* leaf (e.g. extracts of Teavigo™, Teavigo™ phospholipids (epigallocatechin gallate (EGCG)), shiso extract, *Pureraria mirifica* extract, luteolin (e.g., *Perilla ocymoides* leaf extract), astilbin, extracts or derivatives of vitamin E (e.g. Vital ET™ or disodium lauraminodipropionate tocopheryl phosphate), amentoflavone, tetrahydropiperine (e.g. Cosmoperine™), lichochalcone (LR15 (glycyrrhiza inflata root extract)), astaxanthin, *Brassica juncea* extract (e.g., Phytavail™ Zn), red clover extract, unfermented green rooibos extract, enzyme CoQ-10, salvia extract (e.g. an extract of *Salvia miltorrhiza*), ximenynic acid extract, hops oleoresin extract, apple extract, soy extract, saw palmetto extract, or ellagic acid extract, wherein administration of the composition inhibits proteasomal activity.

In a further embodiment, the effective amount of any one of the above identified ingredients comprising the compositions of the present invention and used in the methods of the present invention ranges from 0.01% to 10% of the total composition.

In one aspect of the present invention, there is provided a method of increasing secretion of vascular endothelial growth factor, keratinocyte growth factor, or both from dermal papilla cells that comprises administering a composition to dermal papilla cells. The composition includes lichochalcone, extract of unfermented green rooibos (*Aspalathus linearis*), extract of saw palmetto (*Seronoa repens* or *Sabal serrulata*), extract of shiso (*Perilla frutescens*), and an acceptable carrier, wherein the lichochalcone, extract of unfermented green rooibos, extract of saw palmetto and extract of shiso increase dermal papilla cell secretion of vascular endothelial growth factor, keratinocyte growth factor, or both.

In this aspect, the composition may include from about 0.01% to about 5% by weight lichochalcone, or from about 0.1% to about 2.5% lichochalcone, or from about 0.2% to about 1% lichochalcone, or from about 0.2% to about 0.5% lichochalcone, and in one embodiment the lichochalcone is present at about 0.25%. The composition may include from about 0.01% to about 5% by weight of an extract of unfermented green rooibos (*Aspalathus linearis*) (also referred to within this specification as "green rooibos"), or from about 0.1% to about 2% green rooibos, or from about 0.5% to about 1.5% green rooibos, or from about 0.75% to about 1.25% green rooibos, and in one embodiment the green rooibos is present at about 1%. In certain aspects, the green rooibos may be present in an amount between from about 0.1% to about 1%. The composition may include from about 0.01% to about 5% by weight saw palmetto, or from about 0.1% to about 2.5% saw palmetto, or from about 0.2% to about 1% saw palmetto, or from about 0.4% to about 0.6% saw palmetto, and in one embodiment the saw palmetto is present at about 0.45%. The composition may include from about 0.01% to about 5% by weight shiso, or from about 0.1% to about 2.5% shiso, or from about 0.5% to about 2% shiso, or from about 1% to about 1.5% shiso, and in one embodiment the shiso is present at about 1.25%.

In another alternative embodiment, the present invention is a composition or method of using the composition for regulating the production of melanin in skin and/or hair, wherein the composition comprises one or more of the following ingredients in an effective amount: *boswellia serrata* extract (e.g. frankincense), Boswellin Forte®, boswin 30 (5-loxin), *Undaria pinnatifida* extract (e.g. an extract of brown algae such as GFS 75%), extracts of green tea or extracts of *Camellia sinensis* leaf (e.g. extracts of Teavigo™, Teavigo™ phospholipids (epigallocatechin gallate (EGCG)), shiso extract, *Pureraria mirifica* extract, luteolin (e.g., *Perilla ocymoides* leaf extract), astilbin, extracts or derivatives of vitamin E (e.g. Vital ET™ or disodium lauraminodipropionate tocopheryl phosphate), amentoflavone, tetrahydropiperine (e.g. Cosmoperine™), lichochalcone (LR15 (glycyrrhiza inflata root extract)), astaxanthin, *Brassica juncea* extract (e.g., Phytavail™ Zn), red clover extract, unfermented green rooibos extract, enzyme CoQ-10, salvia extract (e.g. an extract of *Salvia miltorrhiza*), ximenynic acid extract, hops oleoresin extract, apple extract, soy extract, saw palmetto extract, or ellagic acid extract.

BRIEF DESCRIPTION OF THE DRAWING

FIG. 1 shows the VEGF protein expression of a composition according to the present invention in comparison to other individual ingredients.

DETAILED DESCRIPTION

It is to be understood that this invention is not limited to the particular methodology or protocols described herein. Further, unless defined otherwise, all technical and scientific terms used herein have the same meaning as commonly understood to one of ordinary skill in the art to which this invention belongs. It is also to be understood that the terminology used herein is for the purpose of describing particular embodiments only, and is not intended to limit the scope of the present invention, which will be limited only by the claims.

The present invention relates to novel compositions and methods for preventing or decreasing the loss of hair and/or stimulating or increasing hair growth. The present invention is a unique composition of ingredients comprising extracts of one or more of the following: *boswellia serrata* extract (e.g. frankincense), Boswellin Forte®, boswin 30 (5-loxin), *Undaria pinnatifida* extract (e.g. an extract of brown algae such as GFS 75%), extracts of green tea or extracts of *Camellia sinensis* leaf (e.g. extracts of Teavigo™, Teavigo™ phospholipids (epigallocatechin gallate (EGCG)), shiso extract, *Pureraria mirifica* extract, luteolin (e.g., *Perilla ocymoides* leaf extract), astilbin, extracts or derivatives of vitamin E (e.g. Vital ET™ or disodium lauraminodipropionate tocopheryl phosphate), amentoflavone, tetrahydropiperine (e.g. Cosmoperine™), lichochalcone (LR15 (glycyrrhiza inflata root extract)), astaxanthin, *Brassica juncea* extract (e.g., Phytavail™ Zn), red clover extract, unfermented green rooibos extract, enzyme CoQ-10, salvia extract (e.g. an extract of *Salvia miltorrhiza*), ximenynic acid extract, hops oleoresin extract, apple extract, soy extract, saw palmetto extract, or ellagic acid extract.

In one aspect of the present invention, there is provided a method of increasing secretion of vascular endothelial growth factor, keratinocyte growth factor, or both from dermal papilla cells that comprises administering a composition to dermal papilla cells. The composition includes lichochalcone, extract of unfermented green rooibos (*Aspalathus linearis*), extract of saw palmetto (*Seronoa repens* or *Sabal serrulata*), extract of shiso (*Perilla frutescens*), and an acceptable carrier, wherein the lichochalcone, extract of unfermented green rooibos, extract of saw palmetto and extract of shiso increase dermal papilla cell secretion of vascular endothelial growth factor, keratinocyte growth factor, or both.

In this aspect, the composition may include from about 0.01% to about 5% by weight lichochalcone, or from about 0.1% to about 2.5% lichochalcone, or from about 0.2% to about 1% lichochalcone, or from about 0.2% to about 0.5% lichochalcone, and in one embodiment the lichochalcone is present at about 0.25%. The composition may include from about 0.01% to about 5% by weight of an extract of unfermented green rooibos (*Aspalathus linearis*) (also referred to within this specification as "green rooibos"), or from about 0.1% to about 2% green rooibos, or from about 0.5% to about 1.5% green rooibos, or from about 0.75% to about 1.25% green rooibos, and in one embodiment the green rooibos is present at about 1%. In certain aspects, the green rooibos may be present in an amount between from about 0.1% to about 1%. The composition may include from about 0.01% to about 5% by weight saw palmetto, or from about 0.1% to about 2.5% saw palmetto, or from about 0.2% to about 1% saw palmetto, or from about 0.4% to about 0.6% saw palmetto, and in one embodiment the saw palmetto is present at about 0.45%. The composition may include from about 0.01% to about 5% by weight shiso, or from about 0.1% to about 2.5% shiso, or from about 0.5% to about 2% shiso, or from about 1% to about 1.5% shiso, and in one embodiment the shiso is present at about 1.25%.

Further with respect to this aspect, the present invention may include a composition that consists essentially of the above specified amounts of each of lichochalcone, extract of unfermented green rooibos (*Aspalathus linearis*), extract of saw palmetto (*Seronoa repens* or *Sabal serrulata*), extract of shiso (*Perilla frutescens*) together with an acceptable carrier. Another aspect of the invention may include a composition that consists of the above specified amounts of each of lichochalcone, extract of unfermented green rooibos (*Aspalathus linearis*), extract of saw palmetto (*Seronoa repens* or *Sabal serrulata*), extract of shiso (*Perilla frutescens*) together with an acceptable carrier.

The present invention also includes methods of using one or more of these ingredients in a composition for modulating hair growth or regrowth and/or in a composition for regulating melanin production in hair and skin. In one embodiment, the methods of the present invention increase or stimulate hair growth or regrowth and/or prevent or decrease hair loss. In another embodiment, the methods of the present invention reduce or prevent unwanted hair growth or regrowth. In yet a further embodiment, the methods of the present invention modulate the production of melanin in skin and hair.

Hair forms in a pouch-like structure below the skin called a hair follicle. The growth and development of hair follicles is influenced by a number of different growth factors and cytokines, particularly members of the fibroblast growth factor (FGF) family. KGF is a recently identified 28-kd member of the FGF family that induces proliferation of a wide variety of epithelial cells, including keratinocytes.

Visible hair, for example that seen on a human scalp, is actually the hair shaft, which is keratinized, hardened tissue that grows from the hair follicle. In particular, the hair shaft is composed largely of keratin, which is produced by keratinocytes.

Normal hair follicles cycle between a growth stage (anagen), a degenerative stage (catagen), and a resting stage (telogen). Scalp hairs have a relatively long life cycle: the anagen stage ranges from 2 to 6 years, the catagen stage ranges from a few days to a few weeks, and the telogen stage is approximately three months (Fitzpatrick, T. B., et al., eds., Dermatology in General Medicine (Vol. I), McGraw-Hill, Inc., 1993, pp. 290-91; Sperling, L. C., J. Amer. Acad. Dermatology (v. 25 No. 1, Part 1), pp. 1-17 (1991)). Shorter hairs found elsewhere on the human body have corresponding shorter anagen durations. The morphology of the hair and the hair follicle change dramatically over the course of the life cycle of the hair.

During anagen, the hair follicle is highly active metabolically. (Sperling, L. C., J. Amer. Acad. Dermatology (v. 25, No. 1, Part 1), p. 4 (1991)). The follicle comprises a dermal papilla at the base of the follicle; and epidermal matrix cells surrounding the dermal papilla form the base of the hair shaft, which extends upwards from the papilla through the hair canal. (Fitzpatrick, T. B. et al., eds., Dermatology in General Medicine (Vol. I), McGraw-Hill, Inc., 1993). The matrix cells are the actively growing portion of the hair. (Sperling, L. C., J. Amer. Acad. Dermatology (v. 25, No. 1, Part 1), p. 6 (1991)).

At catagen, the matrix cells retract from the papilla, and other degenerative changes occur. (Sperling, L. C., J. Amer. Acad. Dermatology (v. 25, No. 1, Part 1), p. 13-14 (1991)). For example, the vessels and capillaries supplying blood and nutrients to the hair follicle shrivel and stop functioning. A column of epithelial cells pushes the keratinized proximal shaft of the hair upwards (Sperling, L. C., J. Amer. Acad. Dermatology (v. 25, No. 1, Part 1), p. 4 (1991)), and cell death occurs within the follicle. (Fitzpatrick, T. B. et al., eds., Dermatology in General Medicine (Vol. I), McGraw-Hill, Inc., 1993). The hair shaft is then shed from the scalp or other part of the body and the hair follicle enters telogen, the resting stage of the hair growth cycle.

Although hair follicle regulation and growth are not well understood, they represent dynamic processes of proliferation, differentiation, and cellular interactions during tissue morphogenesis. It is believed that hair follicles are formed only in the early stages of development and are not replaced. Thus, an increase in damaged or non-functioning hair follicles is generally associated with hair loss.

For example, impaired vascularization of the hair follicle has been previously suggested to play an important role in the pathogenesis of disorders characterized by hair loss, including androgenetic alopecia (male-pattern hair loss), where baldness is caused by miniaturization, but not loss or abolished cycling, of genetically predisposed follicles. (See e.g., Levy-Frankel (1931) Ann. Dermatol. 10:322-327; Cormia et al., (1961) Arch. Dermatol. 84:772-778. Indeed, the hair follicle dermal papilla, which controls hair growth, is characterized in the anagen phase by a highly developed vascular network but by a non-functioning vascular network in the catagen and telogen phases. Further, expression of an angiogenic growth factor, called vascular endothelial growth factor (VEGF), varies during the hair growth cycle. (Lachgar et al., (1998) Br J. Dermatol. 138(3):407-11)). Specifically, VEGF is highly expressed in dermal papilla cells in the anagen phase, but much less strongly expressed in the catagen and telogen phases.

Additionally, the length and size of hair are dependent on the anagen phase of the hair growth cycle. It has been reported that some cell growth factors, such as VEGF, FGF-5S, insulin-like growth factor-1, and KGF, induce the proliferation of cells in the epidermal matrix, dermal papilla, and dermal papillary vascular system. The proliferation of cells in these areas maintains hair follicles in the anagen phase of the hair growth cycle. In contrast, negative growth factors terminate the anagen phase. If negative growth factors become dominant against cell proliferation growth factors, transforming growth factor beta (TGF-β) evokes apoptosis of matrix cells and shifts the hair follicles from anagen to catagen. This increase in expression of negative growth factors may happen for example, if the hair follicle becomes inflamed due to disease, scarring or some other damage to the hair follicle.

Thus, stimulation of or an increase in expression of various growth factors, such as KGF and/or VEGF, may stimulate or increase hair growth and/or prevent or slow the loss of hair. Similarly, inhibition of inflammation and/or growth factors associated with inducing inflammation may prevent or slow the loss of hair and/or stimulate or increase hair growth or regrowth.

As another example of a damaged or non-functioning follicle being related to hair loss, DHT, formed by the conversion reaction between 5-α reductase and testosterone, may block follicular cellular receptors that signal hair growth, and therefore is associated with hair loss. Further, DHT promotes expression of various caspases, including caspases 3 and 9. Caspases are cysteine proteases which cause cell apoptosis when activated. For example, DHT promotes TGF-β2 which in turn activates caspase 9. Activation of caspase 9 signals downstream activation of caspase 3, which ultimately leads to cell death, particularly apoptosis of keratinocytes. Apoptosis of keratinocytes in turn signals the start of the catagen phase in the hair growth cycle.

Thus, inhibition of DHT, proteases, and/or proteasomes may prevent or slow the loss of hair and/or stimulate or increase hair growth. A proteasome is a noncompartmentalized collection of unrelated proteases which form a common architecture in which proteolytic subunits are self-assembled to form barrel-shaped complexes. The proteasome contains an array of distinct proteases inside a eukaryotic cell.

Compositions of the Present Invention

Hair loss is a very complex disorder. Indeed, as discussed above, many biological factors or mechanisms are known to cause or contribute to hair loss. One advantage of the present invention is that it utilizes unique combinations of ingredients that have been shown to have various effects on biological factors and mechanisms that cause or contribute to hair loss. In particular, the present invention is based on the surprising discovery that the unique combinations of ingredients can be used to stimulate or increase hair growth and/or prevent or slow the loss of hair by having one or more of the following functions: (a) inhibiting the synthesis of DHT; (b) inhibiting proteasomal activity; (c) increasing vascularization; (d) increasing expression of the vascular endothelial growth factor (VEGF); (e) increasing expression of the KGF; (f) inhibiting inflammation; or (g) acting as an antibacterial.

An alternative embodiment of the present invention is based on the surprising discovery that unique combinations of the ingredients described herein can be used to reduce or remove unwanted hairs and hair growth by having one or more of the following functions: (a) increasing the synthesis of DHT; (b) increasing proteasomal activity; (c) suppressing vascularization; (d) suppressing expression and/or secretion of VEGF; or (e) suppressing expression and or secretion of KGF.

An additional alternative embodiment of the present invention is based on another surprising discovery that unique combinations of the ingredients described herein can be used to regulate the production of melanin in skin and hair.

One of ordinary skill in the art will appreciate that many different ingredients, and combinations of those ingredients, may be used in the compositions of the present. For example, a composition of the present invention may comprise an effective amount, e.g. an amount ranging from 0.01-10% by weight of the total composition, of one or more of the following ingredients: *boswellia serrata* extract (e.g. frankincense), Boswellin Forte®, boswin 30 (5-loxin), *Undaria pinnatifida* extract (e.g. an extract of brown algae such as GFS 75%), extracts of green tea or extracts of *Camellia sinensis* leaf (e.g. extracts of Teavigo™, Teavigo™ phospholipids (epigallocatechin gallate (EGCG)), shiso extract, *Purerariа mirifica* extract, luteolin (e.g., *Perilla ocymoides* leaf extract), astilbin, extracts or derivatives of vitamin E (e.g. Vital ET™ or disodium lauraminodipropionate tocopheryl phosphate), amentoflavone, tetrahydropiperine (e.g. Cosmoperine™), lichochalcone (LR15 (glycyrrhiza inflata root extract)), astaxanthin, *Brassica juncea* extract (e.g., Phytavail™ Zn), red clover extract, unfermented green rooibos extract, enzyme CoQ-10, salvia extract (e.g. an extract of *Salvia miltorrhiza*), ximenynic acid extract, hops oleoresin extract, apple extract, soy extract, saw palmetto extract, or ellagic acid extract. These ingredients are described more fully below in Table I.

TABLE I

Ingredients for use in Compositions of the Present Invention

| Ingredient Name: | Characteristics: |
|---|---|
| *Boswellia serrata* extract. | *Boswellia serrata* extracts, such as frankincense, Boswellin Forte ®, and boswin 30 are all boswellic acids, which are known to have anti-inflammatory effects. *Boswellia serrata* is a large, branching deciduous tree which grows abundantly in the dry, hilly parts of India. The gum resin exudates of *Boswellia serrata* have been used in the Ayruvedic system of medicine for the management of rheumatism, respiratory diseases and liver disorders. The major use of *Boswellia serrata* in modern medicine currently is as an anti-inflammatory and anti-arthritic. |
| *Undaria pinnatifida* extract (brown algae) | *Undaria pinnatifida* is a brown algae or seaweed that forms a staple of Japanese and Korea diets. It is known to contain various alginates and antioxidants, such as fucoxanthin. |
| Extracts of green tea | Green tea extracts are known to have antioxidant properties. Phospholipids, such as EGCG, are often present in green tea extracts. Green tea extracts may be obtained, for example, from the leaves of the *Camellia sinensis* plant. |
| Shiso extract | Shiso is an annual member of the mint family. Shiso extracts are obtained from the leaf and stem of the plant. Shiso extract is primarily used to treat inflammatory conditions, such as hay fever, allergies, arthritis, and inflammatory skin diseases. Shiso extracts typically contain the following: monoterpenoids, sesquiterpenoids, alkanes, and phenylpropanoids, flavonoids and rosemarinic acid (1.0-1.2%). |
| *Purerariа mirifica* extract | *Purerariа mirifica* is a plant common to southeast Asia, and is known to have a high melanin formation inhibition characteristic and anti-aging effect. Extracts of *Purearia mirifica* contain phytoestrogens and various isoflavone derivatives that have female hormone effects. |
| Luteolin | Luteolin is an extract that may be derived from leaves of the *Perilla ocymoides* plant. Oral administration of perilla leaf extracts, such as luteolin, is known to have anti-inflammatory and anti-allergic effects. |
| Astilbin | Astilbin is a flavanoid isolated from *Rhizoma Smilacis Glabrae* and is thought to have anti-arthritic effects. |
| Vitamin E and extracts or | Vitamin E, especially in the form of α-tocopherol, is a potent anti-oxidant and is widely used by the body to protect lipids in |

TABLE I-continued

| Ingredients for use in Compositions of the Present Invention | |
|---|---|
| Ingredient Name: | Characteristics: |
| derivatives thereof | cell membranes from oxidative damage. Extracts and derivatives of vitamin E are commercially available as Vital ET ® (disodium lauraminodipropionate tocopheryl phosphate). |
| Amentoflavone | Amentoflavone is a biflavanoid, ubiquitously found in plants, with anti-inflammatory activity. Amentoflavone inhibits TNF, a proinflammatory cytokine that is secreted by activated macrophages and monocytes. |
| Tetrahydropiperine | Tetrahydropiperine, is prepared from piperine, the active principle of black pepper and long pepper. Traditionally, tetrahydropiperine is added to cosmetic products (e.g. lotions, creams, balms, etc.) to improve skin penetration of the products' active compounds. |
| Lichochalcone (e.g., *glycyrrhiza inflata* root extract) | Lichochalcone can be isolated from the roots of licorice, *Glycyrrhiza inflata*, which has various uses in the food and pharmaceutical industries. In particular, lichochalcone has significant antibacterial and anti-inflammatory activities. |
| Astaxanthin | Astaxanthin, a naturally occurring carotenoid pigment, is a powerful biological antioxidant. Astaxanthin exhibits strong free radical scavenging activity and protects against lipid peroxidation and oxidative damage of LDL-cholesterol, cell membranes, cells, and tissues. Astaxanthin is one of a group of natural pigments known as carotenoids. In nature, carotenoids are produced principally by plants and their microscopic relatives, the microalgae. Animals cannot synthesize carotenoids de novo, thus ultimately they must obtain these pigments from the plants and algae that support their food chains (Britton et al. 1995). Commercial production of astaxanthin from the microalgae *Haematococcus pluvialis* is a growing business worldwide, primarily due to the rapid growth of this microorganism and its high astaxanthin content. Other commercial ventures for natural astaxanthin production utilize fermentation of the pink yeast *Xanthophyllomyces dendrorhous* or extraction of the pigment from by-products of crustacea such as the Antarctic krill (*Euphausia superba*). |
| *Brassica juncea* extract | *Brassica juncea* extract is commercially available as Phytavail ™ Zn. Phytavail ™ Zn delivers plant-based minerals with phytonutrient cofactors that are believed to aid in absorption. |
| Red clover extracts | Red clover extracts contain large amounts of isoflavones, a type of phytoestrogen found in a various plants. |
| Unfermented green rooibos extract | Unfermented green rooibos extract is a unique natural extract, derived from the South African plant *Aspalathus linearis*, with a polyphenol content over 25%. |
| Enzyme CoQ10 | CoQ10 is a critical nutrient involved in the production of energy within cells and has been widely used in this country for various cardiac conditions, especially congestive heart failure. |
| Hops oleoresin extract | Hops has a relaxing effect upon the central nervous system, and is used for the treatment of insomnia. It is generally used to relieve tension and anxiety. Oleoresin, an extract from the hops plant, largely consists of humulone, lupulene, estrogenic substances of undetermined structure, tannins, lipids, and xanthohumol (a chalcone). |
| *Salvia* extract | Salvia, an extract of the plant *salvia divinorum*, which is a member of the mint family of plants, or *salvia miltorrhiza*, traditionally was used in religious and healing ceremonies by the Mazatec Indians. |
| Ximenynic acid | Ximenynic acid from white sandalwood seed improves microcirculation and helps to control sebum secretion. It is generally considered an anti-inflammatory and has been used in hair loss treatments. |
| Ellagic acid extract | This extract is a potent antioxidant that typically comes from red raspberries. Recently, ellagic acid has been attributed with significant anti-cancer characteristics. |
| Apple extract | Apple extract typically is composed of 75% polyphenols and is known to have the following effects: suppression of the production of melanin; suppression of the functioning of tyrosine enzymes; skin whitening; alleviating allergic dermatitis; preventing free radical and ultraviolet ray damage to the skin; and providing sun protection. |
| Soy extract | Soy is a staple food in many Asian countries. Soy extract may contain essential amino acids, isoflavones, saponins, and phytosterols. |
| Saw palmetto extract | Saw palmetto is a small, palm like North American plant. Saw palmetto extract typically comes from the berries of the |

TABLE I-continued

| Ingredients for use in Compositions of the Present Invention | |
|---|---|
| Ingredient Name: | Characteristics: |
| | plant and comprises various fatty acids including lauric acid, oleic acid, myristic acid, palmitic acid, and sterols. |

The extracts used in the compositions of the present invention may be obtained from any commercially available source. For example, extracts of *Boswellia serrata* may be purchased as Boswellin® from Sabinsa Corporation (Piscataway, N.J.); green tea extract may be purchased as Teavigo™ from DSM Unlimited (The Netherlands); extracts of vitamin E may be purchased as Vital ET™ from International Specialty Products Corporation (Wayne, N.J.); apple extract may be purchased as Applephenon™ from A.M. Todd Company (Kalamazoo, Mich.); and tetrahydropiperine may be purchased as Cosmoperine™ from Sabinsa Corporation (Piscataway, N.J.).

Alternatively, the extracts used in the compositions of the present invention may be obtained using any known extraction methods. For example, green tea extract can be produced by extracting green tea leaves with an organic solvent. Some examples of organic solvents that might be used in producing the green tea extract to be used in the present invention include hexane, ethyl acetate, ethanol, and hydro-ethanol In another example, solvent sequential fractionation may be used to obtain an extract used in compositions of the present invention. For example, using this technique, the leaves and stems of a shiso plant can be sequentially extracted with hexane, ethyl acetate, ethanol, and hydro-ethanol. The extracts obtained after each step (fractions) of the sequence will contain chemical compounds in increasing order of polarity similar to the solvents used for extracting them. The fractions are dried to evaporate the solvents, resulting in a shiso extract. Those of skill in the art will appreciate that many other solvents can be used in practicing the solvent sequential fractionation extraction of any of the extracts used in compositions of the present invention.

Total hydro-ethanolic extraction techniques might also be used to obtain an extract used in the compositions of the present invention. Generally, this is referred to as a lump-sum extraction of a material of interest, for example lump-sum extraction of red clover leaves. The extract generated in this process will contain a broad variety of phytochemicals present in the material to be extracted, including fat and water solubles. Following collection of the extract, the solvent will be evaporated, resulting in an extract used in the compositions of the present invention.

Total ethanol extraction may also be used in the present invention. This technique also uses plant material to obtain the extract of interest, but ethanol, rather than hydro-ethanol, is the solvent. This extraction technique generates an extract that may include fat soluble and/or lipophilic compounds in addition to water soluble compounds.

Another example of an extraction technique that might be used to obtain one of the extracts used in the compositions of the present invention is supercritical fluid carbon dioxide extraction (SFE). In this extraction procedure the plant material containing the extract of interest is not exposed to any organic solvents. Rather, the extraction solvent is carbon dioxide, with or without a modifier, in supercritical conditions (>31.3° C. and >73.8 bar). Those of skill in the art will appreciate that temperature and pressure conditions can be varied to obtain the best yield of extract. This technique generates an extract of fat soluble and/or lipophilic compounds, similar to the total hexane and ethyl acetate extraction technique described above.

Those of skill in the art will appreciate that there are many other extraction processes, both known in the art and described in various patents and publications that can be used to obtain the extracts to be used in practicing the present invention. For example, the extraction procedures described in the following references, which are incorporated herein by reference, could be used in practicing the present invention: Wang et al., "Extraction and Chromatography-Mass Spectromic Analysis of the Active Principles from Selected Chinese Herbs and Other Medicinal Plants." 2003. Am. J. Chin. Med. 31(6):927-44; Murga et al., "Extraction of natural complex phenols and tannins from grape seeds by using supercritical mixtures of carbon dioxide and alcohol." J. Agric Food Chem. 2000 August:48(8):3408-12; Hong et al., "Microwave-assisted extraction of phenolic compounds from grape seed." Nat Prod Lett. 2001; 15(3):197-204; Ashraf-Khorassani et al., "Sequential fractionation of grape seeds into oils, polyphenols, and procyanidins via a single system employing 002-based fluids." J. Agric Food Chem., 2004 May 5; 52(9): 2440-4.

The compositions of the present invention additionally may contain various known and conventional adjuvants so long as they do not detrimentally affect the hair growth promoting and or hair loss preventing effects provided by the compositions of the present invention. For example, a composition of the present invention can further include one or more additives or other optional ingredients well known in the art, which can include but are not limited to fillers (e.g., solid, semi-solid, liquid, etc.); carriers; diluents; thickening agents; gelling agents; vitamins, retinoids, and retinols (e.g., vitamin B3, vitamin A, etc.); pigments; fragrances; anti-oxidants and radical scavengers; organic hydroxy acids; preservatives; antimicrobial agents; amino acids such as proline, pyrrolidone carboxylic acid, its derivatives and salts, saccharide isomerate, panthenol, buffers together with a base such as triethanolamine or sodium hydroxide; waxes, such as beeswax, ozokerite wax, paraffin wax; plant extracts, such as Aloe Vera, cornflower, witch hazel, elderflower, or cucumber and combinations thereof. Other suitable additives and/or adjuncts are described in U.S. Pat. No. 6,184,247, the entire contents of which are incorporated herein by reference.

The compositions of the present invention can include additional inactive ingredients, including, but not limited to surfactants, co-solvents, and excipients. Particular surfactants can be used based on the on the overall composition of the formulation and the intended delivery of the formulation. Useful surfactants include polyethoxylated ("PEG") fatty acids, PEG-fatty acid diesters, PEG-fatty acid mono- and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, polysaccharide esters, polyethylene glycol alkyl phenols, polyoxyethylene-polyoxypropylene block copolymers, sorbitan fatty acid esters, lower alcohol fatty acid esters, ionic surfactants, and mixtures thereof.

The compositions of the present invention also can include co-solvents such as alcohols and polyols, polyethylene glycols ethers, amides, esters, other suitable co-solvents, and mixtures thereof. The compositions also can include excipients or additives such as sweeteners, flavorants, colorants, antioxidants, preservatives, chelating agents, viscomodulators, tonicifiers, odorants, opacifiers, suspending agents, binders, and mixtures thereof.

Methods of Administration

Compositions of the present invention may be topically administered, orally administered, or any combination thereof. The compositions of the present invention may be prepared, packaged, and labeled for modulation of hair growth or regrowth and/or for modulation of melanin production in skin and hair.

Preferably, the compositions of the present invention are administered with an acceptable carrier. For example, the compositions of the present invention could be externally administered with an acceptable carrier in the form of a gel, lotion, cream, tonic, emulsion, liposome, etc. As a further example, the formulation of the present invention could be internally administered with an acceptable carrier in the form of a pill, tablet, powder, bar, beverage, etc. Thus, the compositions described herein are useful in a wide variety of finished products, including pharmaceutical products, food products, and beverage compositions. Preferably, the products are useful for treating hair loss by preventing or slowing hair loss and/or stimulating or increasing hair growth or regrowth.

Compositions of the present invention may be orally administered in a liquid form such as a solution, syrup, beverage, or suspension. Additionally, compositions of the present invention may be presented as a dried or powdered product for reconstitution with water or other suitable vehicle before use. Liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid).

When administered in the form of a beverage, compositions of the present invention may be water-based, milk-based, tea-based, fruit juice-based, or some combination thereof.

Compositions of the present invention may also be orally administered in the form of a solid prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The solids may be coated by methods well-known in the art. In a preferred embodiment, a composition of the present invention may take the form of a capsule or powder to be dissolved in a liquid for oral consumption. Preparations for oral administration may be suitably formulated to give controlled release of the active compound.

Compositions of the present invention that are orally administered can further comprise thickeners, including xanthum gum, carboxymethyl-cellulose, carboxyethylcellulose, hydroxypropylcellulose, methylcellulose, microcrystalline cellulose, starches, dextrins, fermented whey, tofu, maltodextrins, polyols, including sugar alcohols (e.g., sorbitol and mannitol), carbohydrates (e.g. lactose), propylene glycol alginate, gellan gum, guar, pectin, tragacanth gum, gum acacia, locust bean gum, gum arabic, gelatin, as well as mixtures of these thickeners. These thickeners are typically included in the compositions of the present invention at levels up to about 0.1%, depending on the particular thickener involved and the viscosity effects desired.

Orally administered compositions of the present invention can, and typically will, contain an effective amount of one or more sweeteners, including carbohydrate sweeteners and natural and/or artificial no/low calorie sweeteners. The amount of the sweetener used in the compositions of the present invention will vary, but typically depends on the type of sweetener used and the sweetness intensity desired.

In addition to the compositions described previously, the compounds may also be formulated as a sustained and/or timed release formulation. The compositions must be maintained above some minimum therapeutic dose to be effective. Common timed and/or controlled release delivery systems include, but are not be restricted to, starches, osmotic pumps, or gelatin micro capsules.

The compositions may, if desired, be presented in a pack or dispenser device which may comprise one or more unit dosage forms comprising a composition of the present invention. The pack may for example comprise metal or plastic foil, such as a blister pack. The pack or dispenser device may be accompanied by instructions for administration.

Other useful dosage forms can be prepared by methods and techniques that will be well understood by those of skill in the art and may include the use of additional ingredients in producing tablets, capsules, or liquid dosage forms. The dose, and dose frequency, will vary according to the age, body weight, condition and response of the individual consumer or patient, and the particular composition of the present invention that is used.

Compositions of the present invention also may be topically administered. Thus, in one embodiment of the invention, the compositions of the present invention are topically administered in the form of a: solution, gel, lotion, cream, ointment, oil-in-water emulsion, water-in-oil emulsion, stick, spray, paste, mousse, tonic, liposome or other cosmetically and topically suitable form.

Preferably, compositions of the present invention that are suitable for topical administration are mixed with an acceptable carrier. An acceptable carrier may act variously as a solvent, carrier, diluent or dispersant for the constituents of the composition, and allows for the uniform application of the constituents to the surface of the skin at an appropriate dilution. The acceptable carrier may also facilitate penetration of the composition into the skin.

In one example of a composition for topical application, the acceptable carrier forms from about 90% to about 99.99% by weight of the total composition. In other examples, the acceptable carrier will form from about 97% to 99% by weight of the total composition. The acceptable carrier may also form from about 91% to about 98% by weight of the total composition; from about 92% to about 97% by weight of the total composition; from about 93% to about 96% by weight of the total composition; or from about 94% to about 95% by weight of the total composition. The acceptable carrier can, in the absence of other cosmetic adjuncts or additives, form the balance of the composition.

The various ingredients used in practicing the present invention may be soluble or insoluble in the acceptable carrier. If all ingredients of a formulation are soluble in the acceptable carrier, then the vehicle acts as solvent. One or more of the ingredients used in the compositions of the present invention may be solubilized such that they are soluble in the acceptable carrier. Some examples of solubilizers that may be used in practicing the present invention are water, ethanol, glycerin, various esters and polyethylene glycol derivatives. Alternatively, all or some ingredients of a composition of the present invention may be insoluble in the acceptable carrier. In such a case, those ingredients may be dispersed in the vehicle by means of, for example, a suspension, emulsion, gel, cream or paste, or the like.

Thus, it will be apparent to the skilled artisan that the range of possible acceptable carriers is very broad. For example, acceptable carriers can be emulsions, lotions, creams, or tonics. Acceptable carriers can comprise water, ethanol, butylene glycol, glycerin or other various solvents that aid in penetration of the skin. Some examples of suitable vehicles are described in U.S. Pat. No. 6,184,247 and in U.S. Pat. No. 6,579,516, the entire contents of which are incorporated herein by reference.

Preferably the acceptable carrier used in practicing the present invention comprises water and ethanol. Optionally, the acceptable carrier also contains butylene glycol and/or propylene carbonate. For example, the acceptable carrier can comprise 30-60% water, 45-55% ethanol, 5-10% propylene carbonate, and 5-10% butylene glycol by weight of the composition. In practicing the present invention, preferably this acceptable carrier is mixed with a formulation of the present invention comprising 2% by weight of the total composition. In other embodiments, the acceptable carrier is mixed with a formulation of the present invention comprising 0.99% to 10% by weight of the total composition; 1% to 9% by weight of the total composition; 2% to 8% by weight of the total composition; 3% to 7% by weight of the total composition; or 4% to 6% by weight of the total composition.

In general, however, acceptable carriers according to the present invention may comprise, but are not limited to comprising, any of the following examples: water; ethanol, propylene carbonate, PEG, castor oil; ethylene glycol monobutyl ether; diethylene glycol monoethyl ether; corn oil; dimethyl sulfoxide; ethylene glycol; isopropanol; soybean oil; glycerin; sorbitol; soluble collagen;—

Acceptable carriers in the present invention also may optionally comprise one or more surfactants or solubilizing agents including Ceteareth-20-40, Ianeth-20-40, PEG-35-200 Castor Oil, PEG-35-200, Hydrogenated Castor Oil, PEG-10-80, Sorbitan Laurate, Poloxamer 105-407, and Steareth-21-100. Other examples of surfactants that may be used in practicing the present invention can be found in the CTFA Cosmetic Ingredient Handbook, the relevant portions of which are incorporated herein by reference.

Acceptable carriers in the present invention also may optionally comprise one or more emollients including but not limited to: butane-1,3-diol; cetyl palmitate; dimethylpolysiloxane; glyceryl monoricinoleate; glyceryl monostearate; isobutyl palmitate; isocetyl stearate; isopropyl palmitate; isopropyl stearate; butyl stearate; isopropyl laurate; hexyl laurate; decyl oleate; isopropyl myristate; lauryl lactate; octadecan-2-ol; caprylic triglyceride; capric triglyceride; polyethylene glycol; propane-1,2-diol; triethylene glycol; sesame oil; coconut oil; safflower oil; isoamyl laurate; nonoxynol-9; panthenol; hydrogenated vegetable oil; tocopheryl acetate; tocopheryl linoleate; allantoin; propylene glycol; arachis oil; castor oil; isostearic acid; palmitic acid; isopropyl linoleate; lauryl lactate; myristyl lactate; or decyl oleate Other examples of emollients that may be used in practicing the present invention can be found in the CTFA Cosmetic Ingredient Handbook, the relevant portions of which are incorporated herein by reference.

Other acceptable carriers that may be used in practicing the present invention will be apparent to those of skill in the art and are included within the scope of the present invention.

For example, an acceptable carrier can be a lotion or a gel that is topically applied. The lotion may comprise carbomer, water, glycerin, isopropyl myristate, mineral oil, stearic acid, glycol stearate, cetyl alcohol, dimethicone, preservatives, Triethanolamine and various ingredients of the compositions of the present invention. A gel may comprise water, carbomer, glycerin, propylene glycol, preservatives and various ingredients of the compositions of the present invention.

The compositions of the present invention may also contain various known and conventional cosmetic adjuvants so long as they do not detrimentally affect the desired hair loss preventative or hair growth/regrowth stimulatory properties of the composition. For example, a composition of the present invention can further include one or more additives or other optional ingredients well known in the art, which can include but are not limited to fillers (e.g., solid, semi-solid, liquid, etc.); carriers; diluents; thickening agents; gelling agents; vitamins, retinoids, and retinols (e.g., vitamin B3, vitamin A, etc.); pigments; fragrances; sunscreens and sunblocks; antioxidants and radical scavengers; organic hydroxy acids; exfoliants; skin conditioners; moisturizers; ceramides, pseudoceramides, phospholipids, sphingolipids, cholesterol, glucosamine, pharmaceutically acceptable penetrating agents (e.g., n-decylmethyl sulfoxide, lecithin organogels, tyrosine, lysine, etc.); preservatives; antimicrobial agents; amino acids such as proline, pyrrolidone carboxylic acid, its derivatives and salts, saccharide isomerate, panthenol, buffers together with a base such as triethanolamine or sodium hydroxide; waxes, such as beeswax, ozokerite wax, paraffin wax; plant extracts, such as Aloe Vera, cornflower, witch hazel, elderflower, or cucumber and combinations thereof. Other suitable additives and/or adjuncts are described in U.S. Pat. No. 6,184,247, the entire contents of which are incorporated herein by reference.

Acceptable carriers used in the present invention may optionally comprise one or more penetration enhancers including but not limited to: pyrrolidones, for example 2-pyrrolidone; alcohols, such as ethanol; alkanols, such as decanol; glycols, such as propylene glycol, dipropylene glycol, butylenes glycol; surfactants; glycerol derivatives, or terpenes.

Diffusional resistance of the stratum corneum to topically applied agents has been demonstrated with various compositions for promoting hair growth/regrowth. In order to overcome this barrier effect, a number of compounds can be added to the composition of the present invention to enhance the transdermal delivery of the ingredients of the present invention. Some examples of such compounds include: polyethylene glycol monolaurate; alkyl lactams; long chain amides, substituted 1,2-dioxacyclopentanes and substituted 1,3-diacyclohexanes; 1,4:3,6 dianhydro-2,5-di-o-methyl-D-glucitol; or mixtures thereof.

Other compounds which work to increase circulation to the cells of the scalp also may be added to the compositions of the present invention. These compounds are believed to not only increase health of the cutaneous and subcutaneous tissue of the scalp, but to aid in the delivery and penetration of active components as well. Compounds aiding in circulation which may be used in accord with the teachings herein include, but are not limited to, thistle, *ginkgo biloba*, and peppers (e.g., cayenne and red peppers), ursolic acid (disclosed in Jap. Pat. No. 05286835, and Sattar et al., Pharmazie, 50:62-65 (1995)), or combinations thereof.

Antimicrobials also may be added to the compositions of the present invention. Examples of antimicrobials include, but are not limited to, organic solvents, (e.g. alcohols) and oils or extracts (e.g., oil of wintergreen and peppermint oil), ursolic acid, triclosan, parabens, or combinations thereof.

Some have hypothesized that there is a chronic inflammatory process, subtending to the hair bulbs, in patterned alopecia, leading to eventual scarring of the lower follicle, making regrowth impossible. To counter this inflammatory degenerative process, anti-inflammatories may also be added to the subject compositions. Such anti-inflammatories include steroidal as well as non-steroidal anti-inflammatories. Examples of anti-inflammatory agents useful in accord with the teachings herein include corticosteroids, ibuprofen and derivatives thereof, aspirin and derivatives thereof, aloe vera, shiso extract, ximenynic acid, glycyrrhiza inflata root extract, amentoflavone, boswellia, luteolin and combinations thereof.

The composition of the present invention also can include additional inactive ingredients, including, but not limited to surfactants, co-solvents, and excipients. Surfactants, such as hydrophilic and hydrophobic surfactants, can be included in the compositions. Particular surfactants can be used based on the on the overall composition of the formulation and the intended delivery of the formulation. Useful surfactants include polyethoxylated (PEG) fatty acids, PEG-fatty acid diesters, PEG-fatty acid mono- and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, polysaccharide esters, polyethylene glycol alkyl phenols, polyoxyethylene-polyoxypropylene block copolymers, sorbitan fatty acid esters, lower alcohol fatty acid esters, ionic surfactants, and mixtures thereof.

The compositions of the present invention also can include co-solvents such as alcohols and polyols, polyethylene glycols ethers, amides, esters, other suitable co-solvents, and mixtures thereof. The compositions can also include excipients or additives such as sweeteners, flavorants, colorants, antioxidants, preservatives, chelating agents, viscomodulators, tonicifiers, odorants, opacifiers, suspending agents, binders, and mixtures thereof.

Generally, the compositions of the present invention are topically or orally administered at least on a daily, and preferably a twice daily, basis for a period of time sufficient to bring about the desired level of improvement in modulation of hair growth or regrowth and/or modulation of melanin production in the skin and hair. For example, a user may topically administer a composition of the present invention directly to a balding area or other area where increased hair growth is desired by gently massaging the composition of the present invention into the desired area. This process may be repeated later the same day. Preferably, the composition of the present invention is left on the scalp or other area where increased hair growth is desired between applications occurring on the same day.

Topical application or oral administration of the compositions of the invention may continue for any suitable period of time. For example, within a few weeks to a few months of the initial application or ingestion, a user may notice a reduction in hair loss and/or an increase in hair growth or regrowth. It should be appreciated that the frequency with which the compositions of the present invention should be applied or ingested will vary depending on the desired effect. In particular, the degree of cosmetic enhancement will vary directly with the total amount of composition used.

When topically applied, the compositions of the present invention may be applied to the area to be treated, for example the scalp in humans, by spraying, dabbing, swabbing, or rubbing. For example, in one embodiment, a composition of the present invention may be dispersed in an aerosol form such as in a chlorofluorocarbon solvent, for delivery in spray form. The spray form has many advantages including high loading and enhanced drug uptake. Another advantage of the spray form is that it may be applied more conveniently and without matting the hair in the region of application. Those of ordinary skill in the art will appreciate that other methods may be used to topically administer the compositions of the present invention.

In another embodiment, a composition of the present invention may be provided in a shampoo, conditioner, or other hair product formulation, which preferably may be applied on at least a daily basis. The compositions of the present invention may be added to any shampoo, conditioner, or other hair formulation that is commercially available or commonly used. In one example, a composition of the present invention may be mixed with fatty acid esters or sorbitol and sorbitol anhydrides (commonly called polysorbates). These compounds have nonionic properties that inhibit shedding of hair. Polysorbates are one of a group of nonionic surfactants obtained by esterification of sorbitol with one or three molecules of a fatty acid (e.g. stearic, lauric, oleic, palmitic) under conditions which cause splitting out of water from the sorbitol, leaving sorbitan.

Those of ordinary skill on the art also will appreciate that when topically administered, the compositions of the present invention may be applied periodically on a routine basis prior to, during, and subsequent to modulation of hair growth or regrowth. Generally, the compositions of the present invention will be topically administered on a daily basis, although more frequent applications also may be used.

It is intended that the foregoing detailed description be regarded as illustrative rather than limiting. The present invention is further illustrated by the following experimental investigations and examples, which should not be construed as limiting. The contents of all references, patents and published applications cited throughout this patent are hereby incorporated by reference herein.

EXAMPLES

Example 1

Dihydrotestosterone (DHT) Synthesis by Human Prostate Cells

Dihydrotestosterone (DHT) is a byproduct of the conversion reaction between the enzyme 5-alpha reductase and testosterone. DHT is associated with hair loss because it is known to block several follicular receptors. Therefore, by inhibiting DHT synthesis, it is possible to prevent or slow hair loss.

The ability of each of the ingredients in the compositions of the present invention to inhibit DHT synthesis in human prostate cells was measured. One of ordinary skill in the art will appreciate that there are numerous methods for measuring the ability of a substance to inhibit DHT synthesis. Some examples of such methods are set forth below and described in Lachgar S., et al., 1999. "In vitro main pathways of steroid action in cultured hair follicle cells: vascular approach." J. Invest. Dermatol. Symp. Proc. 4:290-5; and Smith, C M, et al., 1994. "Comparison of testosterone metabolism in benign prostatic hyperplasia and human prostate cancer cell lines in vitro." J. Steroid Biochem. Molec. Biol. 50:151-9, the entire contents of which are incorporated by reference herein.

For example, to measure the ability of a compound to inhibit DHT synthesis, 50 mg of each sample ingredient in powder form was measured. A 100 mg/ml total extract of the sample was then prepared by sequential addition of DMSO: ethanol:water in a ratio of 5:3:2. One of ordinary skill in the art will understand that other amounts of sample may be used. For example, to prepare a 100 mg sample, 1 mL DMSO, 0.6 ml ethanol, and 0.4 ml water are mixed together.

This solution is extensively mixed by vortexing and incubating for 10 minutes in a sonic water bath. Each sample ingredient is diluted from the stock concentration of 50 mg/ml to a test concentration (i.e., typically, 0.1, 1, and 10 μg/ml) in tissue culture media.

The effect of each sample ingredient may be measured using DU-145 cells, which may be purchased from the American Tissue Culture Collection (ATCC) (Manassas, Va.). In particular, the cells are plated at 1×105/well in a standard 24 well tissue culture plate using recommended media such as, for example, Dulbecco's MEM (MEM) with 10% fetal bovine serum. Following plating, the cells are incubated overnight with fresh media containing the diluted sample ingredient. After one to two days of incubation, testosterone is added to the cells at a concentration of 1 nM. The cells are incubated an additional 6 hours at which time the culture supernatant is collected.

DHT expression levels can be measured using a commercially available ELISA kit (Alpha Diagnostic International, San Antonio, Tex.) according to the manufacture's specifications.

One of ordinary skill in the art will appreciate that the methods described above may be used to test the ability of the ingredients of the present invention. The results of analyzing the following sample ingredients using the methods describe above are reported below in Table 2: *boswellia serrata* extract (e.g. frankincense), Boswellin Forte®, boswin 30 (5-loxin), *Undaria pinnatifida* extract (e.g. an extract of brown algae such as GFS 75%), extracts of green tea or extracts of *Camellia sinensis* leaf (e.g. extracts of Teavigo™, Teavigo™ phospholipids (epigallocatechin gallate (EGCG)), shiso extract, *Purerariа mirifica* extract, luteolin (e.g., *Perilla ocymoides* leaf extract), astilbin, extracts or derivatives of vitamin E (e.g. Vital ET™ or disodium lauraminodipropionate tocopheryl phosphate), amentoflavone, tetrahydropiperine (e.g. Cosmoperine™) lichochalcone (LR15 (glycyrrhiza inflata root extract)), astaxanthin, *Brassica juncea* extract (e.g., Phytavail™ Zn), red clover extract, unfermented green rooibos extract, enzyme CoQ-10, salvia extract (e.g. an extract of *Salvia miltorrhiza*), ximenynic acid extract, hops oleoresin extract, apple extract, soy extract, saw palmetto extract, or ellagic acid extract, or any derivative thereof. Data are reported as % control compared to the level of DHT present in cultures of untreated control cells.

TABLE 2

Average % DHT Synthesis Observed:

| Name of Ingredient Tested: | Average % DHT Synthesis Observed: |
|---|---|
| Rogaine (control) | 94.5% |
| *Boswellia serrata* extract | 62.6% |
| Boswellin Forte ® | 70.6% |

TABLE 2-continued

Average % DHT Synthesis Observed:

| Name of Ingredient Tested: | Average % DHT Synthesis Observed: |
|---|---|
| Boswin ™ 30 (5-loxin) | 113.4% |
| *Undaria* (brown algae) | 112.9% |
| Teavigo ™ | 202.2% |
| Teavigo ™ Phospholipids | 103.3% |
| Shiso extract | 78.7% |
| *Purerariа mirifica* extract | 63.7% |
| Luteolin | 96.2% |
| Astilbin | 78.0% |
| Vital ET ™ | 72.1% |
| Amentoflavone | 163.9% |
| Cosmoperine ™ | 130.1% |
| Lichochalcone (LR15 (*glycyrrhiza inflata* root extract)) | 85.0% |
| Astaxanthin | 103.9% |
| Phytavail ™ Zn | 90.5% |
| Red Clover extract | 79.7% |
| Unfermented Green Rooibos extract | 191.3% |
| CoQ10-TPM | 98.3% |
| *Salvia* | 147.0% |
| Ellagic Acid extract | 96.7% |
| Ximenynic Acid extract | 110.2% |
| Hops oleoresin extract | 111.8% |
| Saw palmetto extract (Triarco) | 118.3% |
| Saw palmetto extract (Euromed) | 83.9% |
| Apple extract (Procyanidins) | 90.6% |
| Soy extract (crodasome soyaglycone) | 108.85% |

According to the results reported at Table 2, *Purerariа mirifica* extract, vital ET, and *Boswellia serrata* extract are the most potent inhibitors of DHT synthesis, while Teavigo™ and unfermented green rooibos appear to be the most potent stimulators of DHT synthesis.

Example 2

Growth Factor Secretion by Human Dermal Papilla Cells

The growth and development of hair follicles is influenced by a number of different growth factors and cytokines, particularly members of the FGF family. KGF is a recently identified 28-kd member of the FGF family and is known to play a significant role in hair growth. Another growth factor, VEGF is highly expressed in dermal papilla cells in the anagen phase, but much less strongly expressed in the catagen and telogen phases.

The ability of each of the ingredients in the compositions of the present invention to stimulate or increase secretion of growth factors, such as VEGF and KGF was measured. One of ordinary skill in the art will appreciate that there are numerous methods for measuring the ability of a substance to stimulate secretion of a growth factor. One example of such a method is set forth below and described in Lachgar S., et al., 1998. "Minoxidil upregulates the expression of vascular endothelial growth factor in human hair dermal papilla cells." Br J. Dermatol. 138:407-11, the entire contents of which are incorporated by reference herein.

For example, to measure the ability of a compound to stimulate secretion of a growth factor, 100 mg of each test sample in powder form was measured. A 50 mg/ml total extract of the sample was then prepared by sequential addition of DMSO:ethanol:water in a ratio of 5:3:2. One of ordinary skill in the art will understand that other amounts of sample may be used. For example, to prepare a 100 mg sample, 1 mL DMSO, 0.6 ml ethanol, and 0.4 ml water are mixed together.

This solution is extensively mixed by vortexing and incubating for 10 minutes in a sonic water bath. Each sample ingredient is diluted from the stock concentration of 50 mg/ml to a test concentration (i.e., typically, 0.1, 1, and 10 μg/ml) in tissue culture media.

The effect of each test sample ingredient may be measured using human dermal papilla cells, which may be purchased from Cell Applications (San Diego, Calif.). In particular, the cells are plated at 3.5×104/well in a standard 24 well tissue culture plate using a proprietary medium supplied by the company. Following plating, the cells are incubated overnight. The following day, the media in the wells is aspirated and replaced with fresh media containing the diluted sample ingredient. The cells are again incubated overnight with the samples.

Growth factors in the cell culture supernatants are assayed using commercially available ELISA kits according to the manufacture's specifications. For example, an ELISA assay may be run to detected either KGF, VEGF, or both. An ELISA kit for detecting KGF may be purchased from R&D Systems (Minneapolis, Minn.). An ELISA kit for detecting VEGF may be purchased from Biosource International (Camarillo, Calif.).

One of ordinary skill in the art will appreciate that the methods described above be used to test the ability of the ingredients of the present invention such as, *boswellia serrata* extract (e.g. frankincense), Boswellin Forte®, boswin 30 (5-loxin), *Undaria pinnatifida* extract (e.g. an extract of brown algae such as GFS 75%), extracts of green tea or extracts of *Camellia sinensis* leaf (e.g. extracts of Teavigo™, Teavigo™ phospholipids (epigallocatechin gallate (EGCG)), shiso extract, *Pureraria mirifica* extract, luteolin (e.g., *Perilla ocymoides* leaf extract), astilbin, extracts or derivatives of vitamin E (e.g. Vital ET™ or disodium lauraminodipropionate tocopheryl phosphate), amentoflavone, tetrahydropiperine (e.g. Cosmoperine™), lichochalcone (LR15 (glycyrrhiza inflata root extract)), astaxanthin, *Brassica juncea* extract (e.g., Phytavail™ Zn), red clover extract, unfermented green rooibos extract, enzyme CoQ-10, salvia extract (e.g. an extract of *Salvia miltorrhiza*), ximenynic acid extract, hops oleoresin extract, apple extract, soy extract, saw palmetto extract, or ellagic acid extract, or any derivative thereof, to prevent or slow the loss of hair and/or stimulate or increase hair growth or regrowth.

The results of analyzing the above identified sample ingredients are reported below in Table 3. Data are reported as % control compared to the level of growth factor secreted from untreated control cells.

TABLE 3

| Average % Growth Factor Secretion: | | |
|---|---|---|
| Name of Ingredient Tested: | Average % VEGF Secretion: | Average % KGF Secretion: |
| Rogaine (Control) | 104.1% | 126.2% |
| *Boswellia serrata* extract | 71.7% | 82.0% |
| Boswellin Forte ® | 221.7% | 286.7% |
| Boswin ™ 30 (5-loxin) | 241.1% | 228.4% |
| *Undaria* (brown algae) | 226.5% | 513.3% |
| Teavigo ™ | 108.3% | 245.2 |
| Teavigo ™ Phospholipids | 169.0% | 250.0% |
| Shiso extract | 151.0% | 195.1% |
| Luteolin | 123.2% | 147.8% |

TABLE 3-continued

| Average % Growth Factor Secretion: | | |
|---|---|---|
| Name of Ingredient Tested: | Average % VEGF Secretion: | Average % KGF Secretion: |
| Astilbin | 122.9% | 85.4% |
| Vital ET ™ | 107.9% | 103.0% |
| Amentoflavone | 186.2% | 209.5% |
| Cosmoperine ™ | 172.5% | 75.1% |
| Lichochalcone (LR15 (*glycyrrhiza inflata* root extract)) | 201.0% | 398.3% |
| Astaxanthin | 249.4 | 327.1 |
| Phytavail ™ Zn | 140.5% | 92.9% |
| Red Clover extract | 66.3% | 134.7% |
| Unfermented Green Rooibos extract | 477.7% | 260% |
| CoQ10-TPM | 112.4% | 95.4% |
| *Salvia* extract | 162.6% | 194.5% |
| Ellagic Acid extract | 98.7% | 66.3 |
| Hops oleoresin extract | 130.7% | 138.5% |
| Saw palmetto extract (Triarco) | 237.4% | 346.7% |
| Saw palmetto extract (Euromed) | 106.0% | 127.8% |
| Apple extract (procyanidin B-2) | 93.1% | 142.5% |
| Soy extract (crodasome soyaglycone) | 179.2% | 236% |

According to the results reported at Table 3, unfermented green rooibos extract, Boswin™ 30 (5-loxin), undaria (brown algae), Astaxanthin and Boswellin Forte® are the most potent stimulators of VEGF while undaria (brown algae), unfermented green rooibos extract, Teavigo™, Teavigo™ phospholipids, Licochalcone, and Boswellin Forte® are the most potent stimulators of KGF. Further, according to the results reported at Table 3, red clover extract, and *boswellia serrata* extract appear to be the most potent inhibitors of VEGF secretion while Cosmoperine®, *boswellia serrata* extract, ellagic acid, and astilbin appear to be the most potent inhibitors of KGF secretion.

Example 3

Proteasome Inhibition

The ability of each of the ingredients in the compositions of the present invention to inhibit proteasome activity was measured. One of ordinary skill in the art will appreciate that there are numerous methods for measuring the ability of a substance to inhibit proteasome activity. One example of such a method is set forth below and described in U.S. Pat. No. 6,410,512, the entire contents of which are incorporated by reference herein.

For example, to measure the ability of a compound to inhibit proteasome activity, 100 mg of each test sample in neat form was measured. A 50 mg/ml total extract of the sample was then prepared by sequential addition of DMSO:ethanol: water in a ratio of 5:3:2. One of ordinary skill in the art will understand that other amounts of sample may be used. For example, to prepare a 100 mg sample, 1 mL DMSO, 0.6 ml ethanol, and 0.4 ml water are mixed together.

This solution is extensively mixed by vortexing and incubating for 10 minutes in a sonic water bath. Each sample ingredient is diluted from the stock concentration to a test concentration of 50 mg/ml in proteasome reaction buffer media.

Inhibition of proteasome activity may be assayed using a proteasome kit that is commercially available, for example from Boston Biochem (Boston, Mass.). Test sample ingredients are first added to the proteasome provided with the kit. The fluorescent proteasome substrate is then added and cleavage of the substrate by the proteasome is monitored using a fluorescence plate reader. Data are expressed as % control compared to proteasome activity without any inhibitor or test sample added.

One of ordinary skill in the art will appreciate that the methods set forth in U.S. Pat. No. 6,410,512 may be used to test the ability of the ingredients of the present invention such as, *boswellia serrata* extract (e.g. frankincense), Boswellin Forte®, boswin 30 (5-loxin), *Undaria pinnatifida* extract (e.g. an extract of brown algae such as GFS 75%), extracts of green tea or extracts of *Camellia sinensis* leaf (e.g. extracts of Teavigo™, Teavigo™ phospholipids (epigallocatechin gallate (EGCG)), shiso extract, *Pureraria mirifica* extract, luteolin (e.g., *Perilla ocymoides* leaf extract), astilbin, extracts or derivatives of vitamin E (e.g. Vital ET™ or disodium lauraminodipropionate tocopheryl phosphate), amentoflavone, tetrahydropiperine (e.g. Cosmoperine™), lichochalcone (LR15 (glycyrrhiza inflata root extract)), astaxanthin, *Brassica juncea* extract (e.g., Phytavail™ Zn), red clover extract, unfermented green rooibos extract, enzyme CoQ-10, salvia extract (e.g. an extract of *Salvia miltorrhiza*), ximenynic acid extract, hops oleoresin extract, apple extract, soy extract, saw palmetto extract, or ellagic acid extract, or any derivative thereof, to prevent or slow the loss of hair and/or stimulate or increase hair growth or regrowth.

The results of analyzing the above identified sample ingredients are reported below in Table 4. Data are reported as % control compared to the level of growth factor secreted from untreated control cells.

TABLE 4

Average % Proteasome Activity:

| Name of Ingredient Tested: | Average % Proteasome Activity: |
|---|---|
| Rogaine (Control) | 101.7% |
| *Boswellia serrata* extract | 23.7% |
| Boswellin Forte ® | 23.8% |
| Boswin ™ 30 (5-loxin) | 27.7.0% |
| *Undaria* (brown algae) | 49.5% |
| Teavigo ™ | 17.5% |
| Teavigo ™ Phospholipids | 60.4% |
| Shiso extract | 134.9% |
| *Pureraria mirifica* extract | 91.4% |
| Luteolin | 76.4% |
| Astilbin | 47.7% |
| Vital ET ™ | 68.3% |
| Amentoflavone | 24.5% |
| Cosmoperine ™ | 67.6% |
| Lichochalcone (LR15 (*glycyrrhiza inflata* root extract)) | 23.7% |
| Astaxanthin | 114.0% |
| Phytavail ™ Zn | 113.5% |
| Red Clover extract | 325.1% |
| Unfermented Green Rooibos extract | 92.0% |
| CoQ10-TPM | 103.5% |
| *Salvia* extract | 127.9% |
| Ellagic Acid extract | 44.6% |
| Ximenynic Acid extract | 74.2% |
| Hops oleoresin extract | 73.5% |
| Saw palmetto extract (Triarco) | 96.2% |
| Saw palmetto extract (Euromed) | 102.1% |
| Apple extract (procyanidin B-2) | 73.7% |
| Soy extract (crodasome soyaglycone) | 121.6% |

According to the results reported at Table 4, lichochalcone (LR15 (glycyrrhiza inflata root extract)), amentoflavone, Teavigo™, Boswin 30 and Ellagic acid are the most potent inhibitors of proteasomal activity while red clover extract, shiso extract, salvia extract (e.g. an extract of *Salvia miltorrhiza*), and soy extract appear to be the most potent stimulators of proteasomal activity.

Example 4

A comparison of the hair growth promoting ability was conducted between an extract containing extracts of lichochalcone, green rooibos, saw palmetto and shiso (hereinafter "Test Composition") against that of the minoxidil formulation commercially available as Rogaine® (hereinafter "Minoxidil Composition") over a twelve week period.

The test population in this 12-week study was as follows:

| | # of Subjects Tested | Age | Years Bald | Balding Score |
|---|---|---|---|---|
| Minoxidil Composition | 22 | 29-59 | 13.3 | 5.8 |
| Test Composition | 23 | 18-69 | 11.4 | 5.8 |

The balding score for the test population is based on the Hamilton-Norwood Scale, which is a scale of 1-8 where a higher number corresponds to a greater level of baldness and where 8 represents complete baldness. Each composition was applied twice a day over the entire scalp for 12 weeks.

To compare the hair growth promoting ability of each Composition, a transition zone between the balding and non-balding scalp on each test subject was examined.

To evaluate the effect of each Composition on hair density, a starting measurement was obtained, and after 12 weeks of application of either the Test Composition or the Minoxidil Composition another measurement was obtained. Specifically, at the start and after 12 weeks a digitally captured, magnified (30×) image was obtained and a comparison was made of the summation of pixels relative to total area within a specified region (~2 $cm^2$). With this analysis, the Test Composition showed a 24% average change in hair density compared to baseline while the Minoxidil Composition showed a 25.4% average change. These results demonstrate that no statistically significant difference in performance exists between the Compositions. Both Compositions do, however, exhibit a significant improvement in hair density relative to baseline values.

Example 5

To evaluate the effect of each Composition on the activity of hair follicles, a starting measurement was obtained, and another measurement was obtained after 12 weeks of application of either the Test Composition described in Example 4 or the Minoxidil Composition. Specifically, a digitally captured, magnified (30×) image of an area of interest was obtained and the number of hair follicles in the anagen phase was tabulated and compared to the total number of hair follicles (both active and inactive). From this analysis, we found that the Test Composition achieved a 36.37% average change in the number of Anagen (Active) hair follicles compared to baseline values while the Minoxidil Composition achieved a 27.03% change. These results demonstrate that no statistically significant difference in performance exists between the Compositions. Both Compositions do, however, exhibit a significant improvement in hair density relative to baseline values.

Example 6

To evaluate the effect of each Composition on the hair growth rate, an area of interest was identified and all the hair was shaved down to the scalp. For the next 72 hours, the Compositions were applied to the shaved areas twice every 24 hours. After 72 hours and 6 applications of each Composition, the regrowth was measured from active follicles. From this analysis, it was found that the Test Composition achieved a 11.4% average amount of regrowth compared to baseline values while the Minoxidil Composition achieved a 2.5% average amount of regrowth. These results demonstrate that no statistically significant difference in performance exists between the Compositions. Both Compositions do, however, exhibit a significant improvement in hair density relative to baseline values.

Example 7

A stock sample of each extract ingredient (Saw palmetto, Lichochalcone, Shiso, and Green Rooibos) was prepared by weighing out 100 mg of the extract. The 100 mg of the extract was mixed with a solubilizer comprising DMSO:ethanol: water in a ratio of 5:3:2. Therefore, for 100 mg of neat material, 1 ml DMSO, 0.6 ml ethanol and 0.4 ml water was used. The solution was extensively mixed by vortexing and incubation for 10 minutes in a sonic water bath to form a 50 mg/ml stock concentration of the extract ingredient. The stock concentration was then diluted to the desired test concentration for testing in the tissue culture media. The final concentration of each individual extract ingredient that was tested is shown in the table below.

| Ingredient | Final Concentration tested (μg/ml) |
|---|---|
| Saw Palmetto | 1.8 |
| Lichochalcone | 1 |
| Shiso | 5 |
| Green Rooibos | 0.4 |

A composition containing each of Saw palmetto, Lichochalcone, Shiso, and Green Rooibos was prepared by mixing appropriate amounts of each neat material and combining them with ethanol, water, and other ingredients to form a final composition. The final test concentration was designated KG9299-31 and was tested at a 400 μg/ml so that it contained a final concentration of each extract ingredient that was the same as the final test concentration for each individual extract ingredient as shown in the table below:

| Ingredients | % (w/w) | Final Concentration tested (μg/ml) |
|---|---|---|
| Saw Palmetto | 0.45 | 1.8 |
| Lichochalcone | 0.25 | 1 |
| Shiso | 1.25 | 5 |
| Green Rooibos | 0.1 | 0.4 |
| Ethanol | 20.00 | |
| Water | 65.45 | |
| Other Ingredients | 12.50 | |
| Total | 100.00 | |

Human dermal papilla cells (from a 47 year old Caucasian male) were purchased from Cell Application (San Diego, Calif.) and human keratinocytes were purchased from ATCC (Manassas, Va.). For the assay, the dermal papilla cells were plated at $7.5\times10^3$/well followed by plating of keratinocytes at $4\times10^4$ in standard 96-well tissue culture plates using proprietary medium supplied by the companies. Following plating, the cells were incubated overnight. The following day, the media in the wells was aspirated and replaced with fresh media containing diluted samples. The cells were returned to incubation for 24 hours, after which, the supernatant was isolated and assayed or frozen for future analysis.

Growth factors in the cell culture supernatants were assayed using a commercially available ELISA (enzyme linked immunosorbant assay) kit. The kit for the VEGF ELISA kit was purchased from Biosource International (Camarillo, Calif.). The assay was run according to manufacturers' specifications. Data was reported as concentration (i.e. pg/ml) of growth factor secreted.

Each of 100 μg of the individual extracts (Rooibos, Lichochalcone, Saw Palmetto, and Shiso) and 400 μg of the final composition (KG9299-31) (the combination of each of Saw palmetto, Lichochalcone, Shiso, and Green Rooibos) was tested and compared to a control, ethanol, propylene carbonate, butylenes glycol, oleth 20, dimethyl isosorbide, ethoxydiglycol, and a composition containing only DMSO: ethanol:water. The results are shown in FIG. 1.

FIG. 1 shows that the combination of Rooibos, Lichochalcone, Saw Palmetto, and Shiso demonstrated an increase in VEGF expression at each of the tested levels which was substantially greater than that achieved by each of the individual ingredients alone. This result was unexpected.

The invention claimed is:

1. A method for increasing the secretion of vascular endothelial growth factor, keratinocyte growth factor, or both from dermal papilla cells, said method comprising administering a composition to the dermal papilla cells of a subject in need thereof, said composition comprising from about 0.01% to about 5% by weight licochalcone, from about 0.01% to about 5% by weight unfermented green rooibos extract, from about 0.01% to about 5% by weight saw palmetto extract, and from about 0.01% to about 5% by weight shiso extract.

2. The method of claim 1 wherein the composition comprises from about 0.2% to about 0.5% by weight licochalcone, from about 0.01% to about 1% by weight unfermented green rooibos extract, from about 0.4% to about 0.6% saw palmetto extract, and from about 1% to about 1.5% shiso extract.

3. The method of claim 1, wherein the composition is topically administered.

4. The method of claim 1, wherein the composition further comprises one or more of the following extracts: *Undaria pinnatifida* extract, astaxanthin, *Boswellia serrate* extract, or green tea extract.

5. The method of claim 4, wherein the composition further comprises one or more of the following: *Pueraria mirifica*, luteolin, astilbin, vitamin E, amentoflavone, tetrahydropiperine, red clover, *Brassica juncea*, co-enzyme Q10, *Salvia*, ximenynic acid, hops oleoresin, apple extract, soy extract, or ellagic acid extract.

6. The method of claim 1 wherein the composition increases the secretion of keratinocyte growth factor.

* * * * *